US005847130A

United States Patent [19]

[11] Patent Number: 5,847,130
[45] Date of Patent: Dec. 8, 1998

Sandison

[54] METHOD FOR REDUCING THE NITROSAMINE CONTENT OF N-METHYLMORPHOLINE-N-OXIDE

[75] Inventor: Mark Sandison, Dearborn, Mich.

[73] Assignee: BASF Corporation, Mount Olive, N.J.

[21] Appl. No.: 905,578

[22] Filed: Aug. 4, 1997

Related U.S. Application Data

[62] Division of Ser. No. 702,415, Aug. 14, 1996, Pat. No. 5,693,796.

[51] Int. Cl.[6] .......... C07D 295/24

[52] U.S. Cl. .......... 544/173

[58] Field of Search .......... 544/173

[56] References Cited

U.S. PATENT DOCUMENTS

| | | | |
|---|---|---|---|
| 3,333,000 | 7/1967 | Albert et al. | 564/298 |
| 4,960,934 | 10/1990 | Smith et al. | 544/298 |
| 5,223,644 | 6/1993 | Blezard et al. | 564/298 |
| 5,442,113 | 8/1995 | Blezard et al. | 544/298 |

*Primary Examiner*—Robert W. Ramsuer
*Attorney, Agent, or Firm*—Joanne P. Will

[57] ABSTRACT

Aqueous solutions of N-methylmorpholine N-oxide having reduced nitrosamine concentrations are produced by adding catalytic amounts of inorganic carbonate or bicarbonate or carboxylic acid or carboxylate salt.

5 Claims, No Drawings

METHOD FOR REDUCING THE NITROSAMINE CONTENT OF N-METHYLMORPHOLINE-N-OXIDE

This application is a division of application number 08/702,415, filed Aug. 14, 1996, now U.S. Pat. No. 5,693,796.

FIELD OF INVENTION

The present invention relates to a process for reducing the nitrosamine content of N-methylmorpholine-N-oxide (NMMO) by adding catalytic amounts of inorganic carbonates or carboxylic acids to an aqueous N-methylmorpholine (NMM) solution prior to the addition of hydrogen peroxide.

BACKGROUND

N-Methylmorpholine-N-oxide is a proven solvent for cellulose for the production of cellulose fibers, e.g. U.S. Pat. No. 3,447,939. It is further used as an oxidizing agent in the dihydroxylation of olefins, see, Sharpless et al., J. Am. Chem. Soc. 98 [1976], 1986 and finds utility in intermediate production for pharmaceuticals. The preferred commercial form is an aqueous solution from 50 to 60% in strength.

N-Methylmorpholine-N-oxide, or tertiary amine oxides, in general, are prepared by oxidizing the corresponding amines with hydrogen peroxide, as described in EP 553 552, U.S. Pat. No. 4,247,480, EP 426 084, FR 26 32 638, EP 401 503, U.S. Pat. Nos. 5,055,233, 5,075,501, 5,130,488, EP 307 184, U.S. Pat. No. 4,994,614, EP 320 694, EP 356 918, DE 36 18 352, U.S. Pat. No. 4,748,241, EP 498 346, EP 424 965, U.S. Pat. No. 4,970,341, incorporated by reference herein.

The general reaction scheme for the preparation of NMMO is:

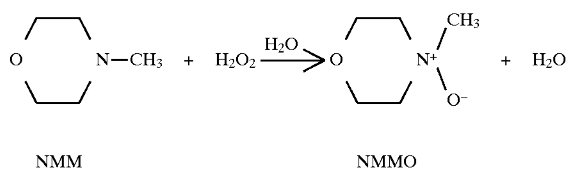

Nitrosamines and colored species are reaction byproducts which negatively impact product quality, even in low concentrations. Nitrosamines are undesirable even in trace amounts because of their carcinogenicity and much effort has been devoted to the suppression of nitrosamine formation, e.g. EP 553,552 ( equivalent to U.S. Pat. No. 5,216,154 ), EP 498,346 (U.S. Pat. No. 5,223,644), U.S. Pat. Nos. 4,994,614, and 5,023,376.

Specifically, EP 553,552 discloses NMMO having below 25 ppb nitrosamines prepared by oxidizing NMM with hydrogen peroxide under a CO2 atmosphere (0–100 psig). EP 498,346 (U.S. Pat. No. 5,223,644) discloses a method for inhibiting nitrosamine formation during amine oxide production (eg NMMO) comprising adding bicarbonates or carbonates in greater than catalytic amounts in the presence of $Na_2EDTA$. U.S. Pat. No. 4,994,614 discloses a method for inhibiting nitrosamine formation during amine oxide production comprising adding a synergistic amount of ascorbic acid and a promoter amount of CO2. U.S. Pat. No. 5,023,376 discloses a method for inhibiting nitrosamine formation comprising adding selected phophonate compounds such as methylenephosphonic acid.

Applicants' have surprisingly discovered that catalytic amounts of inorganic carbonates, bicarbonates, carboxylic acids, and carboxylate salts can be used to reduce the nitrosamine content. This is an improvement in the art because catalytic amounts are considerably smaller than noncatalytic amounts as described in EP 498,346 and no $Na_2EDTA$ is required. Further, the final product NMMO does not have to be filtered because the catalytic amounts of inorganic carbonates, bicarbonates, carboxylic acids, and carboxylate salts are soluble in the NMMO.

SUMMARY

The present invention relates to a process for reducing the nitrosamine content of N-methylmorpholine-N-oxide (NMMO) comprising the steps of:

(a.) obtaining an aqueous N-methylmorpholine solution;

(b.) adding a catalytic amount of an inorganic carbonate or bicarbonate;

(c.) oxidizing the aqueous N-methylmorpholine solution from steps (a) and (b) with hydrogen peroxide at a temperature range from 50°–80° C.;

(d.) adjusting the concentration of the aqueous N-methylmorpholine-N-oxide solution obtained in (c) by distilling off residual N-methylmorpholine and water.

The present invention further relates to a process for reducing the nitrosamine content of N-methylmorpholine-N-oxide (NMMO) comprising the steps of:

(a.) obtaining an aqueous N-methylmorpholine solution;

(b.) adding a catalytic amount of an carboxylic acid or carboxylate salt;

(c.) oxidizing the aqueous N-methylmorpholine solution from steps (a) and (b) with hydrogen peroxide at a temperature range from 50°–80° C.;

(d.) adjusting the concentration of the aqueous N-methylmorpholine-N-oxide solution obtained in (c) by distilling off residual N-methylmorpholine and water.

DETAILED DESCRIPTION

The present invention relates to a process for reducing the nitrosamine content of N-methylmorpholine-N-oxide (NMMO) comprising the steps of:

(a.) obtaining an aqueous N-methylmorpholine solution;

(b.) adding a catalytic amount of an inorganic carbonate or bicarbonate;

(c.) oxidizing the aqueous N-methylmorpholine solution from steps (a) and (b) with hydrogen peroxide at a temperature range from 50°–80° C.;

(d.) adjusting the concentration of the aqueous N-methylmorpholine-N-oxide solution obtained in (c) by distilling off residual N-methylmorpholine and water.

The present invention further relates to a process for reducing the nitrosamine content of N-methylmorpholine-N-oxide (NMMO) comprising the steps of:

(a.) obtaining an aqueous N-methylmorpholine solution;

(b.) adding a catalytic amount of an carboxylic acid or carboxylate salt;

(c.) oxidizing the aqueous N-methylmorpholine solution from steps (a) and (b) with hydrogen peroxide at a temperature range from 50°–80° C.;

(d.) adjusting the concentration of the aqueous N-methylmorpholine-N-oxide solution obtained in (c) by distilling off residual N-methylmorpholine and water.

The NMM raw material used is distilled NMM and preferably the steam distillation azeotrope of N-methylmorpholine/water whose preparation is described in U.S. Pat. No. 4,748,241 incorporated by reference herein.

To the aqueous NMM solution is added a catalytic amount of one of the following materials; inorganic carbonates, inorganic bicarbonates, carboxylic acids, or carboxylate salt. Inorganic carbonates useful in the practice of the present invention include, but are not limited to sodium carbonate, potassium carbonate, lithium carbonate, and ammonium carbonate. Inorganic bicarbonates useful in the practice of the present invention include, but are not limited to, sodium bicarbonate, potassium bicarbonate, lithium bicarbonate, and ammonium bicarbonate. Carboxylic acids useful in the practice of the present invention include, but are not limited to formic acid, acetic acid, propionic acid, butyric acid, and benzoic acid. Carboxylate salts useful in the practice of the present invention include, but are not limited to the sodium, potassium, lithium, and ammonium salts of formic acid, sodium salt of acetic acid, propionic acid, butyric acid, and benzoic acid.

Preferably, a catalytic amount of bicarbonate, carbonate, carboxylic acid, or carboxylate salt is defined as being less than 5.0 mole percent, more preferably less than 2.0 mole percent, most preferably less than 1.0 mole percent relative to the charged NMM. In practice, a catalytic amount of 0.2 mole percent is sufficient to reduce the nitrosamine levels.

The concentration of hydrogen peroxide solution can vary over a wide range. Typically, the hydrogen peroxide solution used will be from 30 to 65% in strength, preferably 50% strength.

The reaction temperature, the hydrogen peroxide addition rate, and the molar ratio of NMM:peroxide can be varied within wide limits. Preference is given to reaction temperatures within the range from 50° C. to 80° C., hydrogen peroxide addition rates of from 100%/hr to 6%/hr of the total amount (based on 100% hydrogen peroxide) for the hydrogen peroxide, and molar ratios of N-methylmorpholine to hydrogen peroxide within the range of 1.43:1.0 to 0.90:1.0.

The aqueous hydrogen peroxide is metered into the NMM solution in a conventional manner. The mixture is stirred until the reaction has ended and the concentration of the crude NMMO solution is then adjusted by distilling off the residual NMMO and water.

Typically, NMMO has a residual nitrosamine level of 120–150 ppb.

A jacketed 1-liter glass reactor equipped with a mechanical stirrer and a stillhead was charged with 464 g of N-methylmorpholine/water azeotrope (73% NMM) and 42 g of deionized water under a nitrogen atmosphere. The NMM solution was heated to 65° C. and 200 g of hydrogen peroxide (50% strength) was metered into the solution over 10 hours. The reaction mixture was held at 65° C. for an additional 6 hours before cooling. The reaction product contained 120 ppb N-nitrosomorpholine (the principle nitrosamine contaminant).

After utilizing the process of the present invention, the nitrosamine levels are substantially reduced as illustrated in nonlimiting Examples 1 and 2.

EXAMPLE 1

A jacketed 1-liter glass reactor equipped with a mechanical stirrer and a stillhead was charged with 464 g of N-methylmorpholine/water azeotrope (73% NMM) and 42 g of deionized water under a nitrogen atmosphere. Inorganic bicarbonate or inorganic carbonate (additive and charges given in TABLE 1) was added to the NMM solution. The NMM solution was heated to 65° C. and 200 g of hydrogen peroxide (50% strength) was metered into the solution over 10 hours. The reaction mixture was held at 65° C. for an additional 6 hours before cooling.

TABLE 1

Effect of inorganic bicarbonate or inorganic carbonate on nitrosamine content.

| Additive | Charge, g | Mole Percent | N-Nitrosomorpholine, ppb |
|---|---|---|---|
| $NaHCO_3$ | 2.7 | 0.96% | <10 |
| $NaHCO_3$ | 2.0 | 0.71% | <10 |
| $NaHCO_3$ | 1.0 | 0.36% | <10 |
| $NaHCO_3$ | 0.5 | 0.18%. | <10 |
| $NaHCO_3$ | 3.4 | 0.96% | 20 |
| $(NH_4)HCO_3$ | 2.6 | 0.98% | <10 |
| $(NH_4)_2CO_3$ | 3.2 | 0.99% | <10 |
| $KHCO_3$ | 3.3 | 0.98% | <10 |
| $Li_2CO_3$ | 2.5 | 1.00% | 80 |

EXAMPLE 2

A jacketed 1-liter glass reactor equipped with a mechanical stirrer and a stillhead was charged with 464 g of N-methylmorpholine/water azeotrope (73% NMM) and 42 g of deionized water under a nitrogen atmosphere. Carboxylic acid or carboxylate salt (additive and charges given in TABLE 2) was added to the NMM solution. The NMM solution was heated to 65° C. and 200 g of hydrogen peroxide (50% strength) was metered into the solution over 10 hours. The reaction mixture was held at 65° C. for an additional 6 hours before cooling.

TABLE 2

Effect of carboxylic acids or carboxylate salts on nitrosamine content.

| Additive | Charge, g | Mole Percent | N-Nitrosomorpholine, ppb |
|---|---|---|---|
| Acetic acid | 1.9 | 0.95% | 30 |
| Acetic acid | 1.0 | 0.50% | 20 |
| Acetic acid | 0.5 | 0.25% | 20 |
| Propionic acid | 2.3 | 0.94% | 20 |
| Benzoic acid | 3.8 | 0.94% | 30 |
| Sodium acetate | 2.6 | 0.95% | 20 |
| Sodium acetate | 1.0 | 0.36% | 40 |

We claim:

1. A process for reducing the nitrosamine content of N-methylmorpholine-N-oxide (NMMO) consisting essentially of the steps of:

(a.) obtaining an aqueous N-methylmorpholine solution;

(b.) adding less than 1.0 mole percent of an inorganic carbonate selected from the group consisting of sodium carbonate, potassium carbonate and lithium carbonate or an inorganic bicarbonate selected from the group consisting of sodium bicarbonate, potassium bicarbonate and lithium bicarbonate;

(c.) oxidizing the aqueous N-methylmorpholine solution from steps (a) and (b) with hydrogen peroxide at a temperature range from 50°–80° C.;

(d.) adjusting the concentration of the aqueous N-methylmorpholine-N-oxide solution obtained in (c) by distilling off residual N-methylmorpholine and water.

2. A process according to claim 1, wherein said catalytic amount is 0.2 mole percent.

3. A process according to claim 1, wherein said inorganic carbonate is sodium carbonate.

4. A process according to claim 1, wherein said inorganic bicarbonate is sodium bicarbonate.

5. A process according to claim 1, wherein said hydrogen peroxide is of 50% strength.

* * * * *